(12) United States Patent
Ehnholm et al.

(10) Patent No.: US 6,493,574 B1
(45) Date of Patent: Dec. 10, 2002

(54) CALIBRATION PHANTOM AND RECOGNITION ALGORITHM FOR AUTOMATIC COORDINATE TRANSFORMATION IN DIAGNOSTIC IMAGING

(75) Inventors: Gösta Jakob Ehnholm, Helsinki (FI); Teuvo J. Vaara, Veikkola (FI); Erkki I. Vahala, Helsinki (FI)

(73) Assignee: Koninklijke Philips Electronics, N.V., Eindhoven (NL)

( * ) Notice: Subject to any disclaimer, the term of this patent is extended or adjusted under 35 U.S.C. 154(b) by 20 days.

(21) Appl. No.: 09/672,719

(22) Filed: Sep. 28, 2000

(51) Int. Cl.[7] ................................................. A61B 5/85
(52) U.S. Cl. ..................... 600/429; 606/130; 378/18; 378/20; 378/207
(58) Field of Search .................. 600/407, 410, 600/417, 424, 425, 429, 437, 473, 476; 606/130; 378/207, 18, 20

(56) References Cited

U.S. PATENT DOCUMENTS

| | | | |
|---|---|---|---|
| 4,791,934 A | 12/1988 | Brunnett | 128/653 |
| 4,793,355 A | 12/1988 | Crum et al. | 128/653 |
| 4,896,673 A | 1/1990 | Rose et al. | 128/660.03 |
| 5,005,578 A * | 4/1991 | Greer et al. | 600/414 |
| 5,230,338 A | 7/1993 | Allen et al. | 128/653 |
| 5,345,540 A | 9/1994 | Schleifer et al. | 395/86 |
| 5,442,672 A | 8/1995 | Picard et al. | 378/20 |
| 5,517,990 A | 5/1996 | Kalfas et al. | 128/653.1 |
| 5,590,655 A | 1/1997 | Hussman | 128/653.1 |
| 5,598,269 A | 1/1997 | Kitaevich et al. | 356/399 |
| 5,682,890 A * | 11/1997 | Kormos et al. | 600/417 |
| 5,776,064 A | 7/1998 | Kalfas et al. | 600/414 |
| 5,787,886 A * | 8/1998 | Kelly et al. | 600/407 |
| 5,799,055 A | 8/1998 | Peshkin et al. | 378/42 |
| 5,921,992 A | 7/1999 | Costales et al. | 606/130 |
| 5,967,982 A | 10/1999 | Barnett | 600/429 |
| 6,052,611 A * | 4/2000 | Yanof et al. | 600/429 |
| 6,069,932 A | 5/2000 | Peshkin et al. | 378/42 |
| 6,076,008 A * | 6/2000 | Bucholz | 600/427 |
| 6,256,529 B1 * | 7/2001 | Holupka et al. | 600/427 |

FOREIGN PATENT DOCUMENTS

| | | |
|---|---|---|
| DE | 19532522 | 3/1997 |
| DE | 19908903 | 9/2000 |
| WO | WO 00 61024 | 10/2000 |

OTHER PUBLICATIONS laserBIRD Precision Optical Tracking Advertisement 11/99.

(List continued on next page.)

*Primary Examiner*—Marvin M. Lateef
*Assistant Examiner*—Jeoyuh Lin
(74) *Attorney, Agent, or Firm*—Fay, Sharpe, Fagan, Minnich & McKee, LLP (57) ABSTRACT

A phantom (50) is positioned on a patient support couch (16) of a diagnostic imaging scanner (10). The phantom includes a plurality of diagnostically imageable elements (52) which are mounted in a fixed relationship such that when projections are made along three orthogonal axes, the projections of the diagnostically elements along each axis are non-overlapping. At least three markers (56) on the phantom are monitored by infrared sensitive cameras (30, 32) or other pick-up devices and the location of the markers in image guided surgery (IGS) space is determined (36). From a priori information about the structure of the phantom, the geometric centers of the imageable elements is determined and projected (64) along the coordinate system axes of IGS space. The phantom is imaged by the diagnostic imaging system to generate projections of the diagnostically imageable elements along each of three coordinate axes of diagnostic image space. By comparing the centers of the imageable elements in the IGS coordinate system with the locations of the centers of the imageable elements in diagnostic image space, a transform between the IGS and image space coordinate systems is determined (66). Subsequent diagnostic images of patient are transformed (68) with the transform from diagnostic image to image guided surgery space.

29 Claims, 2 Drawing Sheets

OTHER PUBLICATIONS laserBIRD Precision Optical Tracking Advertisement 12/99.
laserBIRD Precision Optical Tracking Advertisement 01/00.
Traxtal Technologies Advertising Brochure 09/99.
Printout of Traxtal Web Pages from www.traxtal.com printed Mar. 01, 2000.
Reference–Display System for the Integration of CT Scanning and the Operating Microscope, Chapter 11, Hatch, Oct. 1984, Dartmouth College.

* cited by examiner

CALIBRATION PHANTOM AND RECOGNITION ALGORITHM FOR AUTOMATIC COORDINATE TRANSFORMATION IN DIAGNOSTIC IMAGING

BACKGROUND OF THE INVENTION

The present invention relates to the diagnostic imaging arts. It finds particular application in conjunction with image guided surgery based on magnetic resonance images and will be described with particular reference thereto. However, it is to be appreciated, that it is also applicable to other types of diagnostic imaging procedures, such as CT, nuclear cameras, and the like.

In image guided surgery, a volumetric image of a region of interest of a subject is generated. Based on the medical diagnostic image, a surgical procedure, typically a minimally invasive surgical procedure, is planned. For example, one might determine an optimal path, direction of approach, and depth for a biopsy needle such that the tip of the needle accurately and precisely reaches the tissue to be biopsied without passing through or dangerously close to critical or impenetrable tissues. Once the surgery is planned, the biopsy needle or other surgical instrument is positioned relative to the patient for insertion along the planned trajectory. Of course, the accuracy of the surgical procedure is no better than the accuracy with which the coordinate systems of the patient and the planning image have been aligned and the accuracy with which any variation in their sizes has been scaled.

Various techniques have been utilized to bring the coordinate systems of the patient and the images into coordination. For example, the minimally invasive surgical instrument is sometimes carried by an articulated arm with resolvers, which arm is mounted to the diagnostic imaging system. In this manner, the physical positions of the imaging region and the surgical instrument are mechanically constrained. For greater accuracy and to provide greater flexibility by not requiring permanent mechanical interconnection of the surgical system and the scanner, systems have been added for monitoring the actual position of the surgical instrument in real time. Such instruments typically include infrared lasers, video cameras, acoustic signal generators, radio frequency transmitters, and the like. These systems calculate the actual position of the surgical instrument, in surgical instrument space.

In order to bring the surgical instrument space into coordination with the diagnostic image space, fiducial markers are often employed. For example, three or more fiducial markers, i.e., markers which are both imageable by the diagnostic imaging system and viewable by the real time surgical instrument space monitoring system are attached to a patient prior to imaging. When the diagnostic images are processed, the fiducials appear in the resultant image. By placing a tip of the surgical instrument or other characteristic part of it to each fiducial, the position of the fiducials in both image space and surgical instrument space can be determined. Once determined, the coordinate system and scaling of image space and surgical instrument space can be coordinated. One drawback to this technique is the potential for operator error. First, the fiducials have physical size. When the characteristic part of the surgical instrument is touched to the fiducials, there is the potential for error due to both operator skill and the physical size of the fiducials.

For greater flexibility in the usage of the diagnostic imaging system, the surgical instrument and its real time position monitoring system may not be permanently mounted to the diagnostic scanner. Rather, such systems may be removably mounted to the diagnostic scanner or mounted on movable platforms which are positioned adjacent the diagnostic scanner for use and moved to a remote location or to another scanner when the diagnostic scanner is used for other purposes. Each time the surgical instrument and its monitoring system are positioned or repositioned relative to the scanner, it is advantageous to realign the coordinate systems. To this end, calibration phantoms have been devised which are imageable by the diagnostic imaging system. Such phantoms typically include fiducial-like structures which are imageable by the diagnostic imaging system. The fiducials are also positioned where they can be touched by the characteristic portion of the surgical instrument system. Of course, rather than actually touching each fiducial-like structure, the characteristic part of the surgical instrument system can touch another structure at a known offset from the fiducial-like structure. Once the position of the fiducial-like structures of the calibration phantom are known in both the surgical instrument space and in diagnostic image space, the two coordinate systems can again be coordinated. Again, the accuracy with which the coordinate systems is aligned is dependent upon the skill of the operator in positioning the characteristic point of the surgical instrument and the physical size of the fiducial-like structures.

The present invention contemplates a new and improved automated calibration system which overcomes the above-referenced problems and others.

SUMMARY OF THE INVENTION

In accordance with one aspect of the present invention, a method of coordinating coordinate systems of a diagnostic imaging apparatus and an image guided surgery system is provided. A phantom is positioned in an imaging volume of the diagnostic imaging apparatus. The phantom includes at least three elements which are imageable by the diagnostic imaging apparatus and at least three markers whose location is determinable by the image guided surgery system. The imageable elements are held in a fixed position relative to each other and to the markers in such a manner that there is an a priori relationship between the markers and the imageable elements. A diagnostic imaging procedure is conducted on the phantom to determine locations of the imageable elements in diagnostic image space. The markers are monitored to determine their locations in image guided surgery space. From the a priori relationship between the markers and the imageable elements of the phantom, either the locations of the imageable elements in image guided surgery space are determined from the determined locations of the markers or the locations of the markers in diagnostic image space are determined from the locations of the imageable elements of the phantom. The determined locations of either the imageable elements or the markers in image guided surgery space are compared with the determined locations of the same in diagnostic image space and a coordinate transform for transforming between the determined locations in image guided surgery and diagnostic image space is determined.

In accordance with another aspect of the present invention, a phantom for coordinating a diagnostic image coordinate system of diagnostic image coordinate space and an image guided surgery coordinate system of image guided surgery space is provided. The phantom includes at least three diagnostically imageable elements which are bound in a polymeric binder. At least three markers which are monitorable by the image guided surgery system are mounted on the polymeric binder.

In accordance with another aspect of the present invention, an apparatus for coordinating coordinate systems of a diagnostic imaging apparatus and an image guided surgery system is provided. The diagnostic imaging apparatus non-invasively analyzes structure in an imaging region and generates electrical signals indicative thereof. A phantom which has at least three elements which are imageable by the diagnostic imaging apparatus and at least three markers with an a priori known relationship with the imageable elements is positioned in the imaging region. Cameras view at least the markers and generate electrical signals indicative thereof. An image guided surgery processor determines locations of the markers from the electrical signals from the cameras. A processor determines the locations of the imageable elements in image guided surgery space from the locations of the markers. A projection processor projects the determined locations of the imageable elements in image guided surgery space along each of three mutually orthogonal axes. An image reconstruction processor reconstructs the electrical signals from the diagnostic imaging apparatus into diagnostic image representations and into projection images along each of three mutually orthogonal axes to generate projection images in diagnostic image space. A coordinate system alignment transform processor compares the locations of the imageable elements in the projections in image guided surgery space and the projections in diagnostic image space and determines a transform between diagnostic image and image guided surgery space therefrom. A transform processor transforms the diagnostic image representations from diagnostic image space into image guided surgery space for display on a monitor.

One advantage of the present invention is that it provides for an automatic, machine implemented coordination of coordinate systems.

Another advantage of the present invention is that it eliminates variations in results due to variations in operator skill levels.

Another advantage of the present invention is that it provides for one-click coordinate calibration.

Another advantage of the present invention resides in the automatic generation of error and accuracy determinations.

Still further advantages reside in increased accuracy, repeatability, reliability, and simplicity.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not be construed as limiting the invention.

DETAILED DESCRIPTION OF THE PREFERRED EMBODIMENTS

Figure 1:
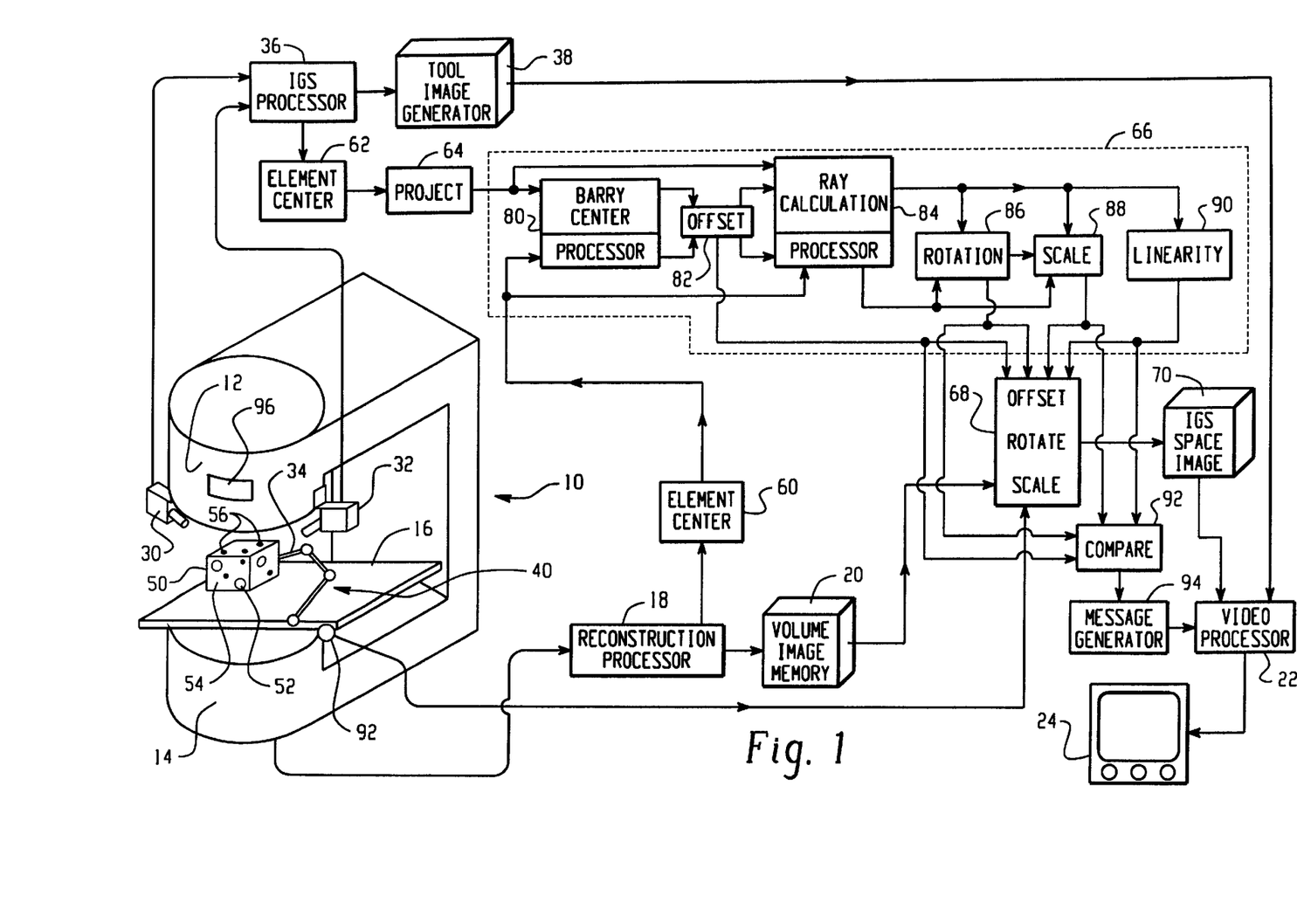
FIG. 1 is a diagrammatic illustration of a magnetic resonance imaging and image guided surgery system in accordance with the present invention; and, FIG. 2 is a perspective view of a calibration phantom in accordance with the present invention.

With reference to FIG. 1, a magnetic resonance scanner 10 includes a pair of pole pieces 12, 14 between which a magnetic field is generated. A patient support couch 16 supports a patient or other object to be imaged in the magnetic field. Gradient and radio frequency coils (not shown) are mounted on the poles. The gradient magnetic field coils with associated drivers induce gradient magnetic fields across an imaging region. The radio frequency coils with associated transmitters and receivers induce and manipulate magnetic resonance in the imaging region and receive magnetic resonance signals emanating therefrom. The radio frequency signals are digitized and conveyed to a reconstruction processor 18. The reconstruction processor, using two-dimensional inverse Fourier transform or other conventional imaging techniques, reconstructs the resonance signals into a volumetric image representation of the imaging region which is stored in a volume image memory 20. The volumetric image representation is in image space, i.e., in an image coordinate system with image scaling. A video processor 22 extracts selected image data from the volume image memory 20, such as slices, surface renderings, slab images, flow images, and the like, and converts them into appropriate format for display on a human-readable display 24 such as a video monitor or active matrix display.

An image guided surgery system includes at least two receivers 30, 32 for receiving signals from a surgical tool 34. In the preferred embodiment, the receivers 30, 32 are infrared sensitive video cameras which receive infrared light reflected from a plurality of infrared radiating dots or structures on the surgical tool. The infrared can be reflected from infrared reflective dots or emitted by infrared emitters. The infrared receivers are connected with an image guided surgery processor 36 which calculates the position and orientation of the surgical tool, in image guided surgery space. Image guided surgery space is defined by an image guided surgery coordinate system and scaling. The processor 36 is connected with an image generator 38 for generating an image of the surgical tool in image guided surgery space. The video processor 22 is connected with the image generator 38 to enable a representation of the surgical tool to be superimposed on displayed images.

The surgical tool 34 can be operated freehand by the operator. The processor 36 continuously updates and recalculates its position in image guided surgery space. Alternately, the surgical tool 34 can be connected with an articulated arm assembly 40 or other mechanical structures for facilitating positioning it and holding it in a fixed position. The articulated arm 40 includes pivot joints which contain resolvers and releasable locks. From the resolvers, the position and orientation of the surgical tool is readily determined. Once the position of the surgical tool in image-guided surgery space is determined by the receivers 30, 32 and the processor 36, a processor associated with the resolvers can determine new positions of the surgical tool in image guided surgery space.

Figure 2:
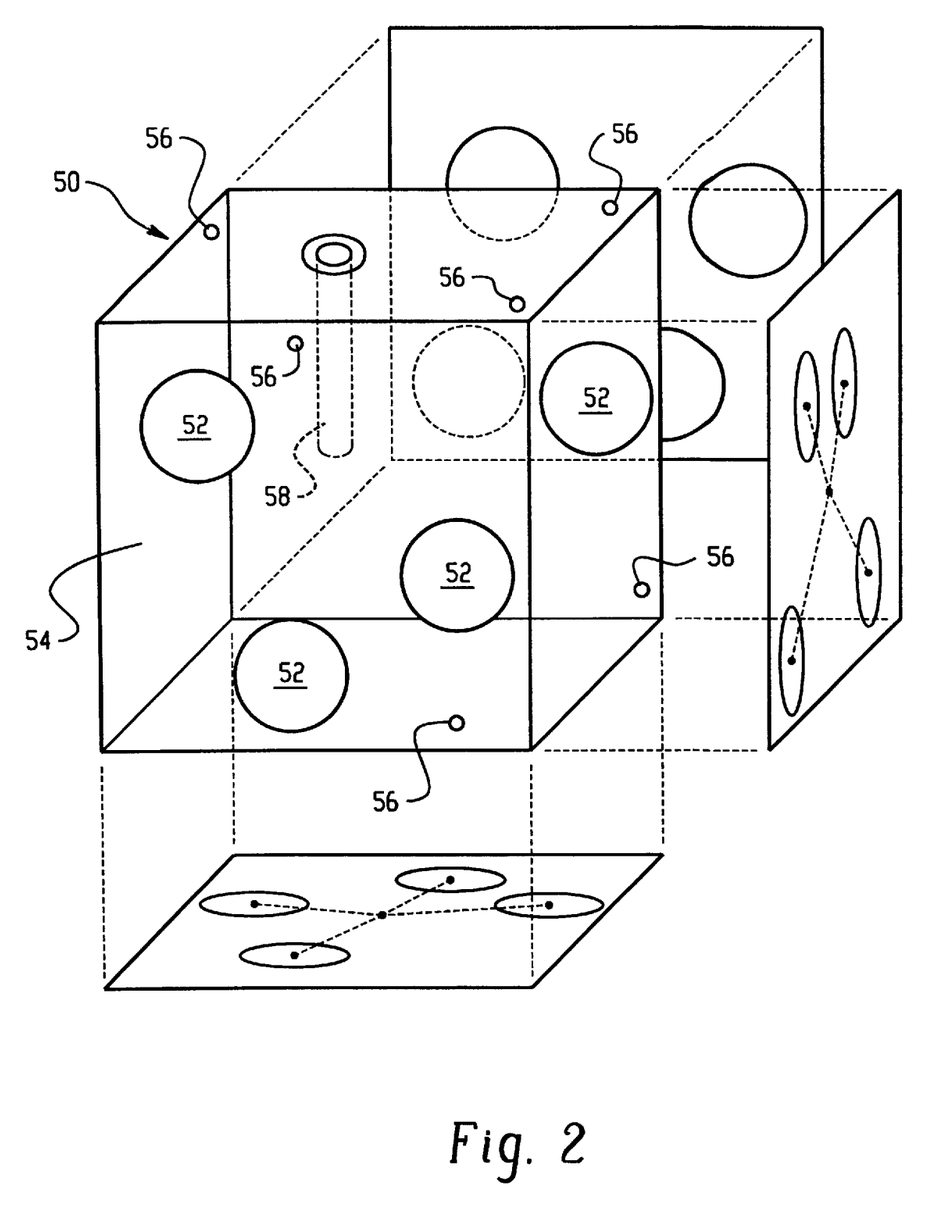

With continuing reference to FIG. 1, and particular reference to FIG. 2, a phantom 50 is positioned in a known location on the patient support couch 16. The phantom includes at least three and preferably four or more diagnostically imageable markers 52 which are encased in a diagnostically imageable substantially transparent binder 54. In the preferred magnetic resonance imaging embodiment, the markers are water filled containers, preferably spheres for simplicity of mathematical calculations to determine the geometric centers or other characteristic points. The imageable markers are positioned such that in projections along each of three mutually orthogonal directions, at least three markers are clearly visible and not superimposed. Analogously, at least three and preferably four or more markers or emitters 56 are carried by binder 54. In the preferred infrared embodiment, the markers are spheres, e.g., 1 cm in diameter, preferably circular for simplicity of mathematical calculation, which reflect infrared light to the infrared receivers or cameras 30, 32. Other types of characteristically light reflective or light, sound, or radio frequency emitting markers may be utilized.

Because both the imageable elements 52 and the markers 56 are held in a mechanically, fixed relationship to each other by the binder 54, their relative positions and relationships are fixed. More specifically, once the positions of one of the imageable elements and the markers are determined, the positions of the other is known.

Once the phantom 50 is stationarily positioned on the patient support 16 in the imaging volume, a series of three projection imaging sequences is run. That is, the phantom is imaged in such a manner that the reconstruction processor 18 reconstructs three projection images, each along one of the coordinate axes of the coordinate system of image space. An imageable element center calculator 60 calculates the geometric center of each of the imageable elements 52. In this manner, each of the imageable elements is reduced to a point in image space.

The image guided surgery processor 36 determines the position of the geometric centers of the markers 56. An image element location processor 62, from a priori knowledge of the relationship between the markers and the imageable elements, converts the coordinates of the markers into the coordinates of the centers of the imageable elements in image guided surgery space. A projection processor 64 projects the centers of the imageable elements in image guided surgery space along each. of the three axes of the image guided surgery coordinate system of image guided surgery space. A coordinate system coordinating processor 66 analyzes the image guided surgery space and image space projection images to calculate a transform between image guided surgery and image space. In the illustrated exemplary embodiment, the transform determines shift or offset along each axis, rotation about each axis, and a scaling factor along each axis. Because the imaging system and the surgical instrument produce outputs in absolute units, the transforms should be unity. If they differ significantly from unity, an error message is generated. The offset, rotation, and scaling factors are loaded into a volume image adjustment processor 68 which transforms data from the diagnostic volume image memory 20 from the diagnostic image coordinate system into the image guided surgery coordinate system. Optionally, a second volume memory 70 is provided to store a volumetric image representation transformed to the coordinate system of image guided surgery space.

By way of an exemplary coordinate system coordination processor, a barry center processor 80 calculates the barry center of each of the six projection images. The barry center can be conceptualized as the center of mass if an element of equal mass were positioned directly on the center of each of the imageable elements. An offset processor 82 compares the location of the barry center in the most similarly oriented projection image in image space and in image guided surgery space. In this manner, the offset processor determines and outputs an offset by which each element of image data is to be shifted when being transformed from image space to image guided surgery space. Once the barry centers are aligned, a ray calculation processor 84 calculates the direction of rays from the barry center to the center of the imageable elements in each of the six projection images with their barry centers aligned. A rotation processor 86 calculates the amount of rotation along each axis which brings the rays of the image space projection images into alignment with the rays of the image guided surgery space projection images. A scaling processor 88 determines an amount by which the rays of image space need to be scaled to match the ray length in image guided surgery space. Outputs from the offset processor 82, the rotation processor 86, and the scaling processor 88 are conveyed to a comparitor 90. If the comparitor 90 determines that they differ from unity by more than a preselected tolerance, an error message generator 92 generates an error message advising the operator of the nature of the misalignment. Optionally, this process can be iteratively repeated to optimize the alignment.

Once the offset, rotation, and scaling factor memory 68 is loaded, the phantom 50 is removed from the scanner and a patient or other subject to be examined is positioned on the patient support 16. The patient is imaged to generate a three-dimensional diagnostic image which is offset, rotated and scaled by the processor 68, and stored in image guided surgery space volume memory 70. Thereafter, all displays of the image data on the monitor 24 are in the coordinate system of the image guided surgery system.

When the surgical tool is supported by an articulated arm that has its own processor for calculating the position and orientation of the surgical instrument, the coordinate system of the surgical instrument is readily aligned with the rest of the image guided surgery system. For example, the tool can be positioned touching a preselected point on the phantom. From the data collected in the calibration process described above, the preselected point on the phantom is known with precision in the image guided surgery coordinate system. The self-contained coordinate position calculation system of the articulated arm can then be set to this same reference coordinate.

When doing biopsies, a needle is mechanically attached to the articulated arm assembly 40. Often, the free length of the needle between the point of attachment and its tip is not known. Because the needle is to be kept sterile, measuring or calibrating this length is difficult. To this end, the phantom is provided with a well 58 for receiving the needle point. The well, which is removable for sterilization, receives the needle tip with a known trajectory and end termination point. In this way, the position of the tip relative to the phantom is fixed. The position of the arm, particularly the mechanism for engaging the needle, is monitored in image guided surgery space. Because the exact location of the end of the well was previously known in image guided surgery space from the analysis of the phantom, the exact length of the needle is now known.

When a large number of imageable elements are disposed in the phantom, the coordinate system alignment processor 66 also includes a non-linearity processor 94 which determine non-linearities along each axis in the transform between the coordinate systems. In this manner, non-linearities, such as non-linearities due to variations in the main magnetic field can be corrected by the coordinate transform processor 68. The comparitor 90 compares the determined non-linearity with preselected non-linearity criteria. The display generator 92 generates excess non-linearity warnings.

Typically, magnetic resonance imaging systems have laser gauging systems which mark the center or other preselected planes or points relative to the imaging volume, i.e., relative to the diagnostic image. By placing the phantom accurately relative to the laser gauging system, the laser guiding system can be aligned with the image guided surgery coordinate system and error signals generated.

Analogously, the patient support couch 16 is typically movable in a horizontal plane along two orthogonal axes. As the patient support couch is shifted, the shift along the longitudinal and transverse axes relative to a zero point is displayed on a display 96. The transform processor 68 is connected with a monitor 92 for monitoring patient support couch movement to maintain offsets in the coordinate system as the patient is moved. The accuracy of the measurement of patient couch movement can be determined with using the above-discussed calibration technique in each of two or more positions along the longitudinal and transverse axes. If the offsets determined by the alignment processor 66 do not match the distances measured by the couch movement measurement system, the couch movement measurement system is recalibrated accordingly. Similar adjustments can be made for vertical couch movement.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of coordinating coordinate systems of a diagnostic imaging apparatus and an image guided surgery system, the method comprising:

positioning a phantom in an imaging volume of the diagnostic imaging apparatus, which phantom includes at least three elements which are imageable by the diagnostic imaging apparatus and includes at least three markers whose location is determinable by the image guided surgery system, the imageable elements being held in a fixed position relative to each other and to the markers such that there is an a priori relationship between the markers and the imageable elements;

conducting a diagnostic imaging procedure on the phantom to determine locations of the imageable elements in coordinates of diagnostic image space;

monitoring the markers to determine locations of the markers in coordinates of image guided surgery space;

from the a priori relationship between the markers and the imageable elements, determining one of: (1) the locations of the imageable elements in image guided surgery space from the determined locations of the markers, and (2) the locations of the markers in diagnostic image space from the locations of the imageable elements;

comparing the determined locations of one of the markers and the imageable elements in an image guided surgery space and diagnostic image space and determining a coordinate transform for transforming between the determined locations in image guided surgery space and diagnostic image space.

2. The method as set forth in claim 1 further including:

removing the phantom from the diagnostic imaging volume;

placing a subject to be imaged in the diagnostic imaging volume;

conducting a diagnostic imaging procedure to generate a volumetric diagnostic image representation in diagnostic image space;

operating on the volumetric diagnostic image representation with the transform to transform the diagnostic image representation into image guided surgery space.

3. The method as set forth in claim 2 wherein conducting a diagnostic imaging procedure on the phantom includes:

generating projection diagnostic images along three mutually orthogonal axes of diagnostic image space.

4. The method as set forth in claim 3 wherein determining the coordinate transform includes:

determining the location of the imagaeble elements in image guided surgery space.

5. The method as set forth in claim 4 further including:

generating projections of the imageable elements in image guided surgery space along three mutually orthogonal axes of image guided surgery space.

6. The method as set forth in claim 5 wherein the coordinate transform determining step compares the three projections in image guided surgery space with the three projections in image space to determine the transform therebetween.

7. The method as set forth in claim 2 further including:

monitoring a surgical tool in image guided surgery space; and, generating a human-readable image from the image guided surgery space diagnostic image with a representation of the surgical tool superimposed thereon.

8. The method as set forth in claim 2 further including:

after determining the locations in image guided surgery space, shifting a position of the phantom along at least one axis with a subject support couch;

measuring a distance of movement with the patient support couch;

repeating the monitoring step;

repeating the locations determining step;

finding a distance between the determined locations before and after the phantom was shifted;

comparing a distance from a patient couch distance measuring system with the determined distance.

9. The method as set forth in claim 1 wherein the phantom includes a polymeric binder within which the imageable elements are bound and on the surface of which the markers are attached.

10. The method as set forth in claim 9 wherein the polymeric binder material is formed in a rectangular prism.

11. A method of coordinating coordinate systems of a diagnostic imaging apparatus and an image guided surgery system, the method comprising:

positioning a phantom in an imaging volume of the diagnostic imaging apparatus, which phantom includes at least three elements which are imageable by the diagnostic imaging apparatus and includes at least three markers whose location is determinable by the image guided surgery system, the imageable elements being held in a fixed position relative to each other and to the markers such that there is an a priori relationship between the markers and the imageable elements;

conducting a diagnostic imaging procedure on the phantom to determine locations of the imageable elements in coordinates of diagnostic image space;

monitoring the markers to determine locations of the markers in coordinates of image guided surgery space;

from the a priori relationship between the markers and the imageable elements, determining one of: (1) the locations of the imageable elements in image guided surgery space, and (2) the locations of the markers in diagnostic image space;

comparing the determined locations of one of the markers and the imageable elements in image guided surgery space and diagnostic image space and determining a coordinate transform for transforming between the determined locations in image guided surgery space and diagnostic image space; and, in response to the comparing step, generating a misalignment message.

12. A method of coordinating coordinate systems of a diagnostic imaging apparatus and an image guided surgery system, the method comprising:

positioning a phantom in an imaging volume of the diagnostic imaging apparatus, which phantom includes at least three elements which are imageable by the diagnostic imaging apparatus and includes at least three markers whose location is determinable by the image guided surgery system, the imageable elements being held in a fixed position relative to each other and to the markers such that there is an a priori relationship among the markers and the imageable elements;

conducting a diagnostic imaging procedure on the phantom to determine locations of the imageable elements in diagnostic image space;

monitoring the markers to determine locations of the markers in image guided surgery space;

determining one of: (1) the locations of the imageable elements in image guided surgery space from the a priori relationship among the markers and the imageable elements, and from the determined locations of the markers, and (2) the locations of the markers in diagnostic image space from the a priori relationship among the markers and the imageable elements, and from the locations of the imageable elements;

comparing the determined locations of one of the markers and the imageable elements in an image guided surgery space and diagnostic image space and determining a coordinate transform for transforming between the determined locations in image guided surgery space and diagnostic image space; and, generating a message indicative of the determined coordinate transform.

13. A method of coordinating coordinate systems of a diagnostic imaging apparatus and an image guided surgery system, the method comprising:

positioning a phantom in an imaging volume of the diagnostic imaging apparatus, which phantom includes at least three elements which are imageable by the diagnostic imaging apparatus and includes at least three markers whose location is determinable by the image guided surgery system, the imageable elements being held in a fixed position relative to each other and to the markers such that there is an a priori relationship between the markers and the imageable elements;

conducting a diagnostic imaging procedure on the phantom that generates phantom projections along three mutually orthogonal axes of diagnostic imaging space;

monitoring the markers to determine locations of the markers in coordinates of image guided surgery space;

from the a priori relationship between the markers and the imageable elements, generating projections of the imageable elements in image guided surgery space along three mutually orthogonal axes of image guided surgery space;

comparing the determined locations of one of the markers and the imageable elements in an image guided surgery space and diagnostic image space and determining a coordinate transform for transforming between the determined locations in image guided surgery space and diagnostic image space by locating the imageable elements in image guided surgery space by comparing the three phantom projections in image guided surgery space with the three phantom projections in image guided surgery space and determining an offset factor, a rotation factor, and a scaling factor of a transform between image guided surgery space and diagnostic image space;

removing the phantom from the diagnostic imaging volume;

placing a subject to be imaged in the diagnostic imaging volume;

conducting a diagnostic imaging procedure on the subject that generates a volumetric diagnostic image representation in diagnostic image space;

operating on the volumetric diagnostic image representation with the transform to transform the diagnostic image representation into image guided surgery space.

14. The method as set forth in claim 13 wherein the locations of the imageable elements in image guided surgery space are a geometric center of each element in image guided surgery space and further including:

from the diagnostic image space projections, determining a geometric center of each imageable element.

15. A method of coordinating coordinate systems of a diagnostic imaging apparatus and an image guided surgery system, the method including:

positioning a phantom in an imaging volume of the diagnostic imaging apparatus, which phantom includes at least three imageable elements which are imageable by the diagnostic imaging apparatus in diagnostic image space and includes at least three optical markers, different from imageable elements, whose location is determinable by the image guided surgery system in image guided surgery space, the imageable elements being held in a fixed position relative to each other and to the markers such that there is an a priori relationship between the markers and the imageable elements;

conducting a diagnostic imaging procedure on the phantom to determine locations of the imageable elements in coordinates of diagnostic image space;

optically monitoring the markers to determine locations of the markers in coordinates of image guided surgery space;

determining one of:
(1) the locations of the imageable elements in image guided surgery space from the determined locations of the markers, and the a priori relationship between the markers and the imageable elements, and,
(2) the locations of the markers in diagnostic image space from the locations of the imageable elements, and the a priori relationship between the markers and the imageable elements, comparing the determined locations of one of:
the markers in image guided surgery space and diagnostic image space, and,
the imageable elements in image guided surgery space and diagnostic image space; and from the comparing of the determined of the determined locations in image guided surgery space and diagnostic image space, determining a coordinate transform for transforming between the determined locations in image guided surgery space and diagnostic image space;

moving a preselected portion of a surgical instrument into contact with a preselected touch point location on the phantom with a preselected angle of approach to the touch point location relative to the phantom;

from an a priori relationship between the preselected touch point location and the optical markers, coordinating a coordinate system of the surgical instrument with a coordinate system of image guided surgery space.

16. The method as set forth in claim 15 wherein the surgical instrument includes a biopsy needle which is mounted to an articulated arm and further including:

inserting a tip of the biopsy needle into a sterilized well in the phantom, the touch point location being at the bottom of the well;

while the tip of the biopsy needle is touching the touch point at the bottom of the well, determining a location of the articulated arm in image guided surgery space;

from the location of the tip of the biopsy needle and the location of the articulated arm, determining a length of the biopsy needle.

17. A method of coordinating coordinate systems of a magnetic resonance imaging apparatus and an image guided surgery system, the method comprising:

positioning a phantom in an imaging volume of the magnetic resonance imaging apparatus, which phantom includes at least three elements which are magnetic resonance imageable by the diagnostic imaging apparatus and includes at least three markers whose location is determinable by the image guided surgery system, the imageable elements being held in a fixed position relative to each other and to the markers such that there is an a priori relationship among the markers and the imageable elements;

generating a magnetic field through the imaging volume, which magnetic field has non-linearities which cause distortions in determined locations of the imageable elements conducting a magnetic resonance imaging procedure on the phantom to determine locations of the imageable elements in the coordinate system of diagnostic image space;

monitoring the markers to determine locations of the markers in the coordinate system of image guided surgery space;

determining one of: (1) the locations of the imageable elements in image guided surgery space from the determined locations of the markers and the a priori relationship between the markers and the imageable elements, and (2) the locations of the markers in diagnostic image space from the locations of the imageable elements, and the a priori relationship between the markers and the imageable elements;

from the determined locations of one of: (1) the markers in image guided surgery space and diagnostic image space and (2) the locations of the imageable elements in image guided surgery space and diagnostic image space, and determining a coordinate transform for transforming between the coordinate systems of image guided surgery space and diagnostic image space;

with the coordinate transform, transforming locations of the imageable elements from diagnostic image space to image guided surgery space;

comparing the relative position of the imageable elements in image guided surgery space with the a priori relationship of imageable markers;

in response to the comparing step, determining if the determined locations of the imageable elements in diagnostic image space is distorted; and, generating a distortion message.

18. A phantom for coordinating a diagnostic image coordinate system of a diagnostic image space and an image guided surgery coordinate system of an image guided surgery space, the phantom comprising:

at least three diagnostically imageable elements;

a polymeric binder within which the diagnostic imageable elements are bound in a fixed spatial relationship with each other; and, at least three markers, separate from the three diagnostically imageable elements, which are monitorable by the image guided surgery system, the markers being mounted on the polymeric binder in a fixed spatial relationship with the diagnostically imageable elements and each other, the markers being invisible to a diagnostic imaging system that images the imageable elements.

19. The phantom as set forth in claim 18 wherein the imageable elements are positioned such that along each of three mutually orthogonal axes, projections of the imageable elements are non-overlapping.

20. The phantom as set forth in claim 18 wherein the polymeric binder material is configured in a rectangular prism.

21. The phantom as set forth in claim 18 further including a well removably received in the polymeric binder.

22. An apparatus for coordinating coordinate systems of a diagnostic imaging apparatus and an image guided surgery system, the apparatus comprising:

a diagnostic imaging apparatus which non-invasively analyzes structure in a diagnostic imaging region and generates electrical signals indicative thereof;

a phantom positioned in the imaging region, the phantom including at least three elements which are imageable by the diagnostic imaging apparatus and at least three optical markers, the optical markers being different than the imageable elements and undetectable by the diagnostic imaging apparatus, there being an a priori relationship among the optical markers and the imageable elements;

optical cameras sensitive to light which view the optical markers and output electrical signals indicative thereof;

an image reconstruction processor for reconstructing the electrical signals from the diagnostic imaging apparatus into an image representation in diagnostic imaging space and for reconstructing projection images representing projections of the imageable elements of the phantom along each of three mutually orthogonal axes;

an image guided surgery system processor which receives the electrical signals from the cameras and determines locations of the optical markers in image guided surgery space;

a processor which determines locations of the imageable elements in image guided surgery space from the locations of the optical markers determined by the image guided surgery system processor and the a priori relationship between the optical markers and the imageable elements;

a projection processor for projecting the locations of the imageable elements in image guided surgery space along each of three mutually orthogonal axes;

a coordinate system alignment transform processor for comparing the projected locations of the imageable elements in image guided surgery space from the projection processor with locations of the imageable elements in the projection images from the reconstruction processor and determining a transform between coordinate systems of image guided surgery space and diagnostic imaging space therefrom.

23. The apparatus as set forth in claim 22 further including:
   a transform processor connected with the coordinate system alignment transform processor and the reconstruction processor for transforming reconstructed diagnostic image representations from diagnostic imaging space to image guided surgery space; and,
   a monitor for converting at least selected portions of the image representation in image guided surgery space into a human readable display.

24. The apparatus as set forth in claim 23 wherein the cameras further monitor a surgical tool and further including:
   a tool image generator for generating an image representation of the tool in image guided surgery space; and
   a processor for superimposing the image representation of the tool on the diagnostic image representation in image guided surgery space and supplying the superimposed image to the monitor.

25. The apparatus as set forth in claim 22 wherein the imageable elements of the phantom are positioned such that along each of the three mutually orthogonal axes, the projections of the imageable elements are non-overlapping.

26. An apparatus for coordinating coordinate systems of a diagnostic imaging apparatus and an image guided surgery system, the apparatus comprising:
   a diagnostic imaging means for non-invasively analyzing structure in a diagnostic imaging region and generating electrical signals indicative thereof;
   a phantom positioned in the imaging region, the phantom including at least three elements which are imageable by the diagnostic imaging means and at least three markers, there being an a priori relationship between the markers and the imageable elements;
   a means for optically viewing the markers and generating output electrical signals indicative thereof;
   an image reconstruction means for reconstructing the electrical signals from the diagnostic imaging means into an image representation in diagnostic imaging space and for generating projections of the imageable elements of the phantom along each of three mutually orthogonal axes in diagnostic image space;
   a means for receiving the electrical signals from the cameras and determining locations of the markers in image guided surgery space;
   a means for determining locations of the imageable elements in image guided surgery space from the determined markers locations and the a priori relationship between the markers and the imageable elements;
   a means for projecting the locations of the imageable elements in image guided surgery space along each of three mutually orthogonal axes;
   a coordinate system alignment means for comparing the projected locations of the imageable elements in image guided surgery space with the imageable element projection in diagnostic image space and determining a transform between image guided surgery space and diagnostic imaging space therefrom; and,
   a message generator means for generating messages indicative of at least one of distortion in the reconstructed image representation, misalignment between image guided surgery space and diagnostic imaging space, and properties of the determined transform.

27. The apparatus as set forth in claim 22 wherein the diagnostic imaging apparatus is a magnetic resonance scanner that generates a magnetic field through the imaging region.

28. An apparatus for coordinating coordinate systems of a diagnostic imaging apparatus and an image guided surgery system, the apparatus comprising:
   a magnetic resonance scanner, which generates a magnetic field through the imaging region, and which non-invasively analyzes structure in a diagnostic imaging region and generates electrical signals indicative thereof;
   a phantom positioned in the imaging region, the phantom including at least three elements which are imageable by the diagnostic imaging apparatus and at least three markers, there being an a priori relationship among the markers and the imageable elements;
   cameras which view the markers and output electrical signals indicative thereof;
   an image reconstruction processor which reconstructs the electrical signals from the diagnostic imaging apparatus into an image representation in diagnostic imaging space and which generates projections of the imageable elements of the phantom along each of three selected axes;
   an image guided surgery system processor which receives the electrical signals from the cameras and determines locations of the markers in image guided surgery space;
   a processor which determines locations of the imageable elements in image guided surgery space from the locations of the markers determined by the image guided surgery system processor and the a priori relationship among the markers and the imageable elements;
   a projection processor for generating projections of the imageable elements in image guided surgery space along each of three selected axes;
   a means for (1) comparing the projections of the imageable elements in image guided surgery space from the projection processor with projections of the image guided elements in diagnostic image space from the reconstruction processor, and (2) determining a transform between image guided surgery space and diagnostic imaging space therefrom, and (3) determining distortion in diagnostic imaging space; and,
   a warning message generator for generating a message indicative of the determined distortion.

29. The method as set forth in claim 1, wherein the markers are substantially invisible to the diagnostic imaging apparatus.

* * * * *